(12) United States Patent
Hill

(10) Patent No.: US 12,708,564 B2
(45) Date of Patent: Aug. 18, 2026

(54) CERUMEN PREVENTION AND REMOVAL DEVICE

(71) Applicant: Michael L. Hill, Cincinnati, OH (US)

(72) Inventor: Michael L. Hill, Cincinnati, OH (US)

( * ) Notice: Subject to any disclaimer, the term of this patent is extended or adjusted under 35 U.S.C. 154(b) by 218 days.

(21) Appl. No.: 18/775,020

(22) Filed: Jul. 17, 2024

(65) Prior Publication Data

US 2025/0025347 A1 Jan. 23, 2025

Related U.S. Application Data

(60) Provisional application No. 63/514,205, filed on Jul. 18, 2023.

(51) Int. Cl.

| | |
|---|---|
| ***A61F 11/00*** | (2022.01) |
| ***A61F 13/15*** | (2006.01) |
| ***A61F 13/38*** | (2006.01) |

(52) U.S. Cl.

CPC ...... *A61F 11/006* (2013.01); *A61F 13/15252* (2013.01); *A61F 13/38* (2013.01)

(58) Field of Classification Search

CPC ... A61F 13/15252; A61F 13/38; A61F 11/006

See application file for complete search history.

(56) References Cited

U.S. PATENT DOCUMENTS

| | | | |
|---|---|---|---|
| 4,329,990 | A | 5/1982 | Sneider |
| 4,707,450 | A | 11/1987 | Nason |
| 5,152,742 | A | 10/1992 | Simpson |
| 6,152,940 | A | 11/2000 | Carter |
| 7,074,230 | B2 | 7/2006 | Olson |
| D560,800 | S | 1/2008 | Curtis |
| 9,549,854 | B1 | 1/2017 | Crespo |

(Continued)

FOREIGN PATENT DOCUMENTS

| | | | |
|---|---|---|---|
| CN | 201185988 | Y | 1/2009 |
| CN | 201205321 | Y | 3/2009 |

(Continued)

OTHER PUBLICATIONS

U.S. Patent and Trademark Receiving Office, International Search Report and Written Opinion of the International Searching Authority, International Application No. PCT/US2024/038322, mailed Dec. 6, 2024 (16 pages).

(Continued)

*Primary Examiner* — Susan S Su
*Assistant Examiner* — Erin A Kim
(74) *Attorney, Agent, or Firm* — Wood Herron & Evans LLP

(57) ABSTRACT

A device for removing and preventing the buildup of cerumen in an ear canal is disclosed. The device includes a body with an elongated handle and a neck portion that extends from the handle to a paddle implement. The neck portion includes one or more crevices and the paddle implement includes a flattened body. The paddle implement is configured to radially deform as the device is rotated in the ear canal during use. The paddle implement is deformable from a radially expanded configuration before use to a radially contracted configuration after use in which the diameter of the paddle implement is smaller compared to the diameter of the paddle when in the radially expanded configuration.

19 Claims, 5 Drawing Sheets

(56) References Cited

U.S. PATENT DOCUMENTS

| | | | | |
|---|---|---|---|---|
| 10,238,545 | B2 | 3/2019 | Kraitzer et al. | |
| 10,449,092 | B2 | 10/2019 | Shuman | |
| 10,813,792 | B2 | 10/2020 | Khademhosseini | |
| 11,134,924 | B2 | 10/2021 | Håkansson et al. | |
| 11,278,709 | B1 | 3/2022 | Mathai et al. | |
| 11,304,850 | B2 | 4/2022 | Kraitzer | |
| 11,324,635 | B2 | 5/2022 | Fahn et al. | |
| D975,270 | S | 1/2023 | Browka | |
| 2001/0001828 | A1 | 5/2001 | Begun | |
| 2006/0085018 | A1 | 4/2006 | Clevenger | |
| 2008/0142385 | A1* | 6/2008 | Stein | A61F 13/38 206/362 |
| 2010/0312198 | A1 | 12/2010 | Guidi | |
| 2011/0066172 | A1 | 3/2011 | Silverstein | |
| 2013/0184684 | A1* | 7/2013 | Yardley | A61F 13/126 606/162 |
| 2019/0321228 | A1 | 10/2019 | Romagnoli | |
| 2020/0214895 | A1 | 7/2020 | Olson | |
| 2021/0401625 | A1 | 12/2021 | Hammers | |
| 2022/0104611 | A1 | 4/2022 | Lebovic et al. | |

FOREIGN PATENT DOCUMENTS

| | | | |
|---|---|---|---|
| CN | 201453497 | U | 5/2010 |
| CN | 106377356 | A | 2/2017 |
| CN | 107224350 | A | 10/2017 |
| CN | 209827229 | U | 12/2019 |
| CN | 110772377 | B | 6/2021 |
| CN | 213465648 | U | 6/2021 |
| CN | 109453004 | B | 7/2022 |
| DE | 20202497 | U1 | 6/2002 |
| DE | 202013103307 | U1 | 10/2014 |
| EP | 3856102 | A1 | 8/2021 |
| FR | 2706288 | B3 | 5/1995 |
| JP | 4768929 | B2 | 9/2011 |
| WO | 2010140144 | A1 | 12/2010 |
| WO | 2020065511 | A1 | 4/2020 |
| WO | 2022187047 | A1 | 9/2022 |

OTHER PUBLICATIONS

International Searching Authority/US, Invitation To Pay Additional Fees And, Where Applicable, Protest Fee, International Application No. PCT/US2024/038322, Sep. 19, 2024 (2 pages).
International Searching Authority/US, Corrected Invitation to Pay Additional Fees and, Where Applicable, Protest Fee, International Application No. PCT/US2024/038322, mailed Oct. 1, 2024 (3 pages).
The International Bureau of WIPO, International Preliminary Report on Patentability, Application No. PCT/US2024/038322, dated Jan. 20, 2026 (11 pages).

* cited by examiner

CERUMEN PREVENTION AND REMOVAL DEVICE

CROSS-REFERENCE TO RELATED APPLICATION

The present application claims the filing benefit of U.S. Provisional Application Ser. No. 63/514,205, filed Jul. 18, 2023, the disclosure of which is incorporated herein by reference in its entirety.

TECHNICAL FIELD

This disclosure relates generally to ear canal hygiene, and more particularly to devices and methods for removing and preventing the buildup of cerumen in the ear canal.

BACKGROUND

The accumulation of cerumen, commonly known as ear wax, in the ear canal is a prevalent problem affecting individuals of all ages. Cerumen is a natural substance produced by the ceruminous glands present in the external auditory canal and may take a dry or wet form. Its purpose is to protect and lubricate the ear canal. Cerumen further prevents the entry of foreign particles into the ear canal, such as dust and insects, and further inhibits the growth of bacteria and fungi.

Maintaining proper ear hygiene is important to a person's health, and the ear has several mechanism for natural self-cleaning to prevent the buildup of cerumen in the ear. For example, the movement of the jaw during activities such as chewing or talking helps to move cerumen gradually from the ear canal to the outer ear. Additionally, the skin lining the ear canal slowly migrates outward, carrying away excess cerumen. However, these natural processes may not be sufficient in every case to prevent the accumulation of cerumen in the ear. In that regard, excessive buildup of cerumen in the ear may lead to a variety of health issues, including hearing loss, discomfort, earache, tinnitus, and in extreme cases, vertigo. Therefore, regular removal of cerumen is essential for ensuring ear health.

Traditionally, the most commonly used method for removing cerumen from the ear canal is the utilization of cotton-tipped swabs, such Q-tips® cotton swabs. However, despite their widespread use, cotton-tipped swabs have several drawbacks and pose potential risks to the ear. For example, when a cotton-tipped swab is inserted into the ear canal, it often pushes the cerumen deeper into the ear rather than removing it. This may result in cerumen becoming compacted in the ear canal, making it more challenging to remove. Additionally, compacted cerumen may cause blockages in the ear canal which may lead to temporary loss of hearing.

Furthermore, the improper use of stiff removal tools, such as cotton-tipped swabs, may damage the delicate structures within the ear, including the eardrum and the skin lining the ear canal. In that regard, cotton-tipped swabs are often used with excessive force, and due to their rigidness, may cause abrasions, cuts, or other injuries to the ear canal. In some cases, the use of cotton-tipped swabs has been associated with ear infections, as they may introduce bacteria into the ear canal, particularly if the cotton tip is contaminated or if the ear canal is scratched during the cleaning process.

Given the limitations and potential risks associated with the use of conventional ear cleaning devices, such as cotton-tipped swabs, there is a clear need for an improved device for safely removing and preventing the buildup of cerumen in the ear canal. In particular, there is a need for a cerumen removal and prevention device that effectively and safely removes cerumen from an ear while minimizing the potential for injury or damage to the ear.

SUMMARY

According to one aspect, a device for removing and preventing the buildup of cerumen in an ear canal is disclosed. The device includes a body that extends between a distal end and a proximal end to define a longitudinal axis of the device. The body includes an elongated handle at the proximal end of the body and a neck portion that extends from the handle to a paddle implement at the distal end of the body. The neck portion includes one or more crevices. The paddle implement includes a flattened body having a measurable width between a first flat surface and a diametrically opposed second flat surface and a height measured between radially peripheral edges of the paddle implement. The width of the paddle implement is less than a diameter of the neck portion and the height of the paddle implement is greater than the diameter of the neck portion. The paddle implement is configured to radially deform as the device is rotated in the ear canal during use. In particular, the paddle implement is deformable from a radially expanded configuration before use to a radially contracted configuration after use in which the diameter of the paddle implement is smaller compared to the diameter of the paddle implement when in the radially expanded configuration.

According to one embodiment, the one or more crevices may comprise one or more spiral crevices that extend circumferentially about the neck portion and along the longitudinal axis of the device. In another embodiment, the body of the device may be formed of a biodegradable material.

According to another embodiment, the paddle implement may be generally S-shaped in transverse cross-section when in the radially contracted configuration. In that regard, the paddle implement may include a first half that extends from the longitudinal axis of the device to a first radially peripheral edge and a second half that extends from the longitudinal axis of the device to a second radially peripheral edge. The first half and the second half of the paddle implement may be curled about the longitudinal axis of the device when in the radially contracted configuration. For example, the first half and the second half of the paddle implement may each be curled in a rotationally opposite direction about the longitudinal axis relative to a rotational direction of the device. The paddle implement may be configured to permanently radially deform as the device is inserted and rotated in the ear canal during use.

According to yet another embodiment, the body of the device may further include an annular flange disposed between the neck portion and the handle. The flange may be configured to limit insertion of the paddle implement into the ear canal. In one embodiment, the paddle implement may be absorbent. Additionally or alternatively, the neck portion may be absorbent. In one embodiment, a portion of the paddle implement or the neck portion may include a color-changing material that is configured to change color when contacted by water or cerumen.

According to one embodiment, at least one of the one or more crevices may extend beyond the neck portion to the paddle implement. For example, the at least one of the one or more crevices may extend onto the first flat surface or the second flat surface of the paddle implement.

According to another embodiment, the paddle implement may be configured to collapse along the longitudinal axis of the device at a predetermined pressure. For instance, the predetermined pressure at which the paddle implement is configured to collapse may within a range of between about 0.1 to about 0.5 psi.

In yet another embodiment, the elongated handle may include a non-absorbent outer coating. For example, the outer coating may include a hardness that is greater than a hardness of the body of the device. Further, the outer coating may be formed of a biodegradable material.

According to another aspect of the invention, a method of using a device for removing and preventing the buildup of cerumen in an ear canal of a user is disclosed. The method includes providing the device according to any of the embodiments described above and inserting the paddle implement into the ear canal. The method further includes rotating the device about the longitudinal axis of the device and in a direction toward a nose of the user to deform the paddle implement and removing the paddle implement from the ear canal. The paddle implement remains deformed once removed from the user's ear canal.

According to another aspect, a method of sizing a device for removing and preventing the buildup of cerumen in an ear canal is disclosed. The method includes measuring a diameter of the outer one-third of the ear canal and providing the device of any of the embodiments described above according to the measured diameter of the outer one-third of the ear canal, with the height of the paddle implement being between 1 mm to 2 mm greater than the diameter of the outer one-third of the ear canal.

According to one embodiment, a length of the neck portion and the implement defines a working length of the device. The method may further include measuring a length of the outer one-third of the ear canal and providing the device according to the length of the outer one-third of the ear canal, with the working length of the device being equivalent to the measured length of the outer one-third of the ear canal.

Various additional features and advantages of the invention will become more apparent to those of ordinary skill in the art upon review of the following detailed description of one or more illustrative embodiments taken in conjunction with the accompanying drawings.

BRIEF DESCRIPTION OF THE DRAWINGS

The accompanying drawings are included to provide a further understanding and are incorporated in and constitute a part of this specification. The drawings illustrate one or more embodiment(s), and together with the description serve to explain principles and operation of the various embodiments. Features and attributes associated with any of the embodiments shown or described may be applied to other embodiments shown, described, or appreciated based on this disclosure.

DETAILED DESCRIPTION

Figure 1:
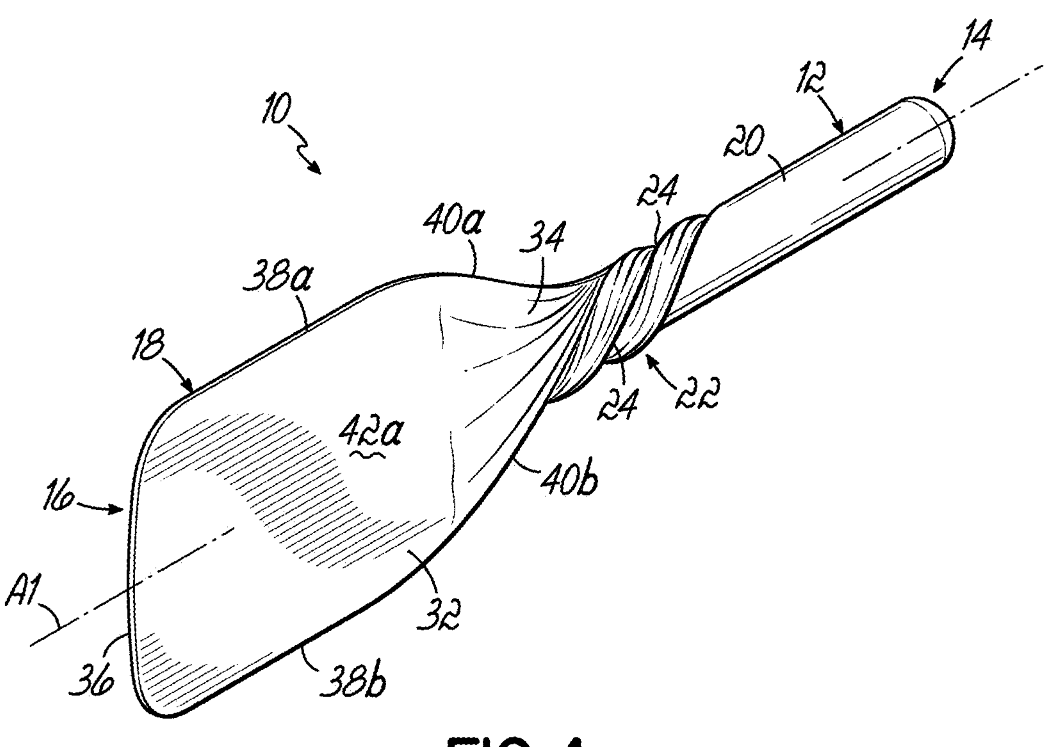
FIG. 1 is a perspective view of a hygiene device for cleaning an ear canal in accordance with an embodiment of the disclosure.
Figure 2:
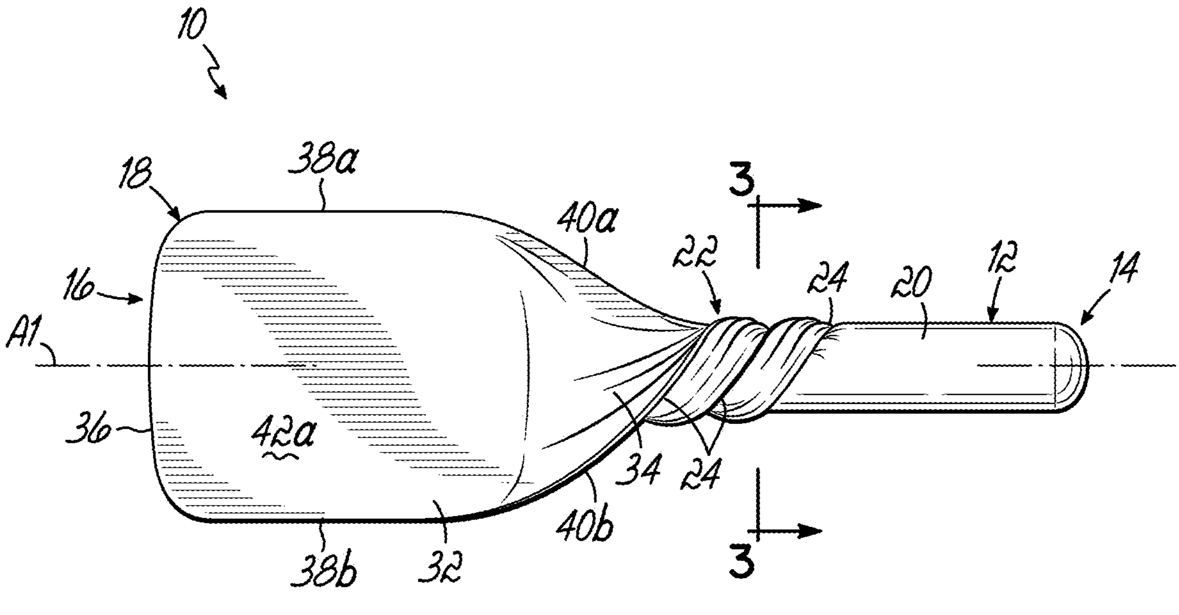
FIG. 2 is a side view of the hygiene device of FIG. 1.

Referring now to the figures, FIGS. 1 and 2 illustrate an ear hygiene device ("device") 10 configured for cleaning an ear canal 11 (e.g., FIG. 6) in accordance with one embodiment of the disclosure. In particular, the device 10 is for preventing the build-up of cerumen and for removing moisture from the outer one-third of the external ear canal 11 safely. In that regard, the device 10 is configured to be inserted into the ear and used to clean and remove small amounts of cerumen, moisture, or other material from the first (i.e., outer) one-third of the ear canal 11. For example, the device 10 may also be used to remove water from the ear canal 11 after taking a shower or bath. The device 10 is made of a soft, pliable material and is configured to remove only small amounts of cerumen, moisture, or other material from the first one-third of the ear canal 11. Thus, some or all parts of the device 10 may be absorbent. The device 10 is configured to deform or collapse when subject to a relatively small amount of force, particularly along the axial direction of the device 10, to prevent impaction of cerumen within the ear. Therefore, the device 10 may be regarded as a wax preventative device that is configured for frequent use, such as daily use, aiming to remove small quantities of cerumen and moisture from the ear. The device 10 is not a corrective device meant for periodically removing substantial amounts of cerumen from the ear. The device 10 may be a single-use device such that after one use, the device 10 may be thrown out. To this end, the device 10 may be formed from one or more biodegradable and/or environment-friendly materials.

With continued reference to FIGS. 1 and 2, the device 10 includes a body 12 that extends between a proximal end 14 and an opposite distal end 16 to define a longitudinal axis A1 of the device 10. The distal end 16 of the body 12 includes an implement 18 that is configured to be disposed within the ear canal 11 during use of the device 10 to clean the ear. The distal end 16 of the body 12 includes a handle 20 configured to be grasped by a user during use of the device 10. The user may use the handle 20 to twist the device 10 once disposed within the ear. In particular, users of the device 10 will be instructed to hold the handle 20 with their thumb and forefinger and to never push the device 10 into their ear further than the handle 20 and their grip of the handle 20 allows. That is, a user's grip on the handle 20 in combination with a length of the handle 20 limits insertion of the device 10 into a user's ear. To prevent over-insertion of the device 10 into a user's ear, the length of the handle 20 may be sized to match a predetermined length measurement of the user's ear canal 11. This ensures that the user cannot push the device 10 further into their ear than the handle 20 allows.

The body 12 further includes a neck portion 22 that extends from the handle 20 to the implement 18. As the device 10 is for cleaning the first one-third of the ear canal 11, a length of the neck portion 22 and the implement 18, otherwise referred to as the working length of the device 10, may correspond to an average length of the outer one-third of an adult ear canal 11. However, other working lengths for the device 10 are possible. For instance, the working length of the device 10 may be individually customized based on a measurement of an individual's ear canal 11. At least the neck portion 22 of the body 12 is flexible to accommodate the various angles of the ear canal 11, which can vary from person to person. For this same reason, the handle 20 and the implement 18 may also be flexible, as will be described in further detail below.

The body 12 of the device 10, which includes the handle 20, the neck portion 22, and the implement 18, may be made from biodegradable materials, or combinations of biodegradable materials, such as bonded paper, paperboard, recycled paper, tissue paper, or other biodegradable products made from fibers such as bamboo fiber, hemp fiber, cotton fiber, or cellulose fiber, for example. The implement 18 or the neck portion 22, or both, may be formed from biodegradable products, such as tissue paper, so as to be absorbent. However, parts of the device 10 may be formed from harder biodegradable materials such as biodegradable plastics, for example.

With continued reference to FIGS. 1 and 2, the handle 20 and the neck portion 22 of the body 12 may each be generally cylindrical in shape. In particular, the neck portion 22 may be an extension of the handle 20, and the neck portion 22 and the handle 20 may have the same diameter, for example. Both the neck portion 22 and the handle 20 may generally have a circular or oval cross-sectional shape. The handle 20 is for gripping the device 10 and includes a generally cylindrical peripheral profile, characterized by smooth, rounded contours. In one embodiment, the handle 20 may include an outer coating that improves the gripability of the handle 20 for holding and twisting the device 10 during use. The outer coating may be non-absorbent and include a hardness that is greater than a hardness of the neck portion 22 and implement 18 of the device 10. The outer coating is biodegradable and may be formed from animal or plant-based materials, such as gelatin, cellulose, or Hypromellose (HPMC), for example. In an alternative embodiment, the handle 20 of the device 10 may be distinct from the body 12 and made from a material that offers greater rigidity compared to the body 12. For example, the handle 20 may be formed from wood, rubber, paperboard, or plastic. In this embodiment, the handle 20 may be made from either a biodegradable or a non-biodegradable material.

As mentioned above, the neck portion 22 is an extension of the handle 20 and extends from the handle 20 to the implement 18. The neck portion 22 may be a linear extension of the handle 20, for example. The length of the neck portion 22 of the device 10 may be varied to achieve the desired overall length of the device 10. This allows for precise sizing of the device 10 to ensure that no part of the device 10 may extend into the ear beyond the outer one-third of the ear canal 11. By varying the length of the neck portion 22, the device 10 may be customized to meet specific requirements of an individual's ear size to provide optimal comfort and safety during use.

As shown in FIGS. 1 and 2, the neck portion 22 includes one or more crevices 24 formed in the neck portion 22. One or more of the crevices 24 may be spiral, extending circumferentially about the neck portion 22 and along the longitudinal axis A1 of the device 10. In the exemplary embodiment shown, the neck portion 22 includes several spiral crevices 24 that extend helically about the neck portion 22 and along the longitudinal axis A1 of the device 10. However, the neck portion 22 may include a single spiral crevice 24 or many more spiral crevices 24, in addition do non-spiral crevices 24, for example. The crevices 24 may vary in size and shape, with most being randomly formed as a result of manufacturing of the device 10. In either case, each spiral crevice 24 is a continuous indent or depression formed in the body 12 of the device 10 that extends a length from the implement 18 to the handle 20. For example, each spiral crevice 24 may extend one or more times about the circumference of the neck portion 22 of the body 12. Each spiral crevice 24 may be a narrow, winding groove or indentation that follows a spiral path, partially or fully about the circumference of the neck portion 22, and each spiral crevice 24 may extend partially or completely between the implement 18 and the handle 20. As will be described in further detail below, the spiral crevices 24 may extend beyond the neck portion 22 to surfaces of the implement 18.

Figure 3:
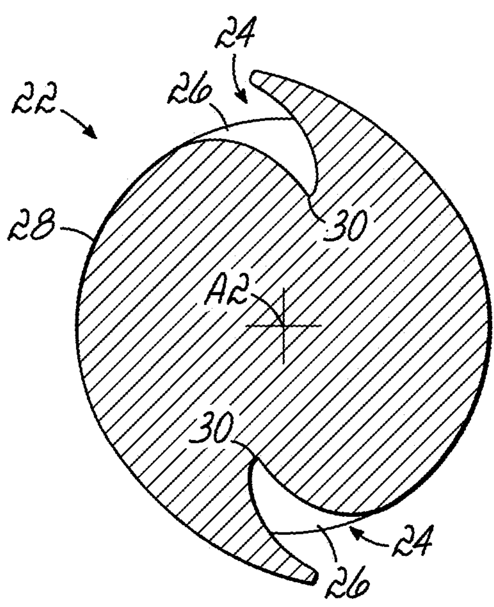
FIG. 3 is a diagrammatic cross-sectional view of the hygiene device taken along line 3-3 of FIG. 2, illustrating exemplary spiral crevices formed in the device in accordance with an embodiment of the disclosure.

FIG. 3 is a diagrammatic cross section of the neck portion 22 of the device 10, illustrating details of two exemplary spiral crevices 24. As shown, each spiral crevice 24 extends a depth from an opening 26 to the crevice 24 formed in an outer surface 28 of the neck portion 22 of the body 12 in a radially inward direction toward the axial center A2 of the neck portion 22 to a base 30 of the spiral crevice 24. The axial center A2 may coincide with the longitudinal axis A1 of the device 10. As shown in FIG. 3, each spiral crevice 24 may be a slit or fold, and be generally V-shaped in transverse cross-section. The outer surface 28 of the neck portion 22 between spiral crevices 24 may be generally smooth or may include crevices or wrinkles. The spiral crevices 24 may be spaced apart evenly about the circumference of the neck portion 22 or randomly spaced.

In one embodiment, the spiral crevices 24 may be formed in the neck portion 22 of the body 12 as a result of twisting the body 12 during manufacturing of the device 10. In that regard, the crevices 24, including the spiral crevices 24, may be randomly formed as a result of wrinkles or crinkles being formed about the neck portion 22 from subjecting the body 12 of the device 10 to a twisting force. By twisting, it is meant that the distal end 16 (or proximal end 14) of the device 10 is rotated in a first direction while the proximal end 14 (or distal end 16) of the device 10 is either held in place or rotated in a second direction that is opposite to the first direction of rotation.

As shown in FIGS. 1 and 2, the implement 18 extends or projects from the neck portion 22 to define the distal end 16 of the device 10. The implement 18 includes a flat, paddle- or spatula-shaped body 32 that is pliable or deformable, allowing the implement 18 to deform as the device 10 is inserted and rotated within the ear canal 11 during use. The body 32 of the implement 18 extends from a base portion 34 adjacent the neck portion 22 to a tip edge 36. The tip edge 36 extends between a pair of peripheral edges 38*a*, 38*b* that define the radially outer extents of the body 32 of the implement 18. The peripheral edges 38*a*, 38*b* are generally parallel to the longitudinal axis A1 of the device 10 and extend from the tip edge 36 to the base portion 34 of the implement 18. The peripheral edges 38*a*, 38*b* may be slightly curved, particularly as they near the tip edge 36. Each peripheral edge 38*a*, 38*b* includes a tapered portion 40*a*, 40*b*, respectively, where the peripheral edge 38*a*, 38*b* transitions to the neck portion 22 of the device 10.

Figure 4:
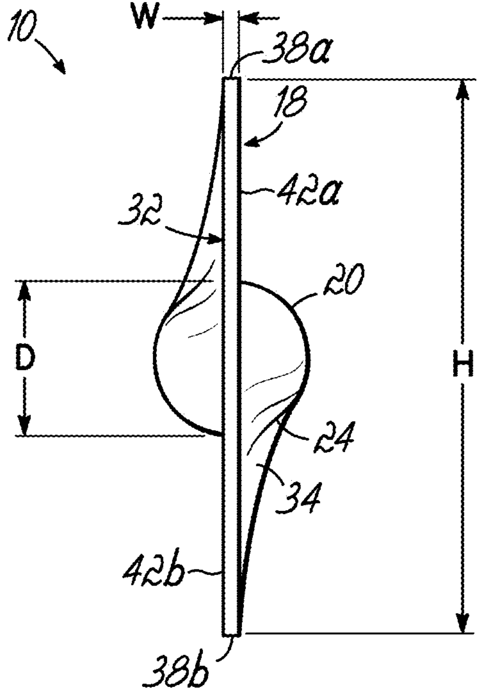
FIG. 4 is a diagrammatic front view of the hygiene device of FIGS. 1-3, illustrating the hygiene device in a radially expanded configuration before use.

As best shown in FIG. 4, the flat body 32 of the implement 18 defines a first generally flat surface 42*a* on one side of the implement 18 and a diametrically opposed second flat surface 42*b* on the other side of the implement 18. In that regard, the body 32 of the implement 18 includes a measurable width W between the first flat surface 42*a* and the second flat surface 42*b*. The body 32 of the implement 18 further includes a measurable height H between the peripheral edges 38*a*, 38*b* of the implement 18. As shown, the width W of the implement 18 is less than a diameter D of the neck portion 22 and the height H of the implement 18 is greater than the diameter D of the neck portion 22. The implement 18 may be generally rectangular in cross-sectional shape. However, the implement 18 may have an S-shaped cross-sectional configuration.

As briefly described above, one or more of the spiral crevices 24 may extend beyond the neck portion 22 of the body 12 to surfaces of the implement 18. As shown in FIGS. 1 and 2, the spiral crevices 24 may extend onto the first or second flat surfaces 42*a*, 42*b* of the body 32, and in particular the base portion 34 of the implement 18. For example, this may be the case when the spiral crevices 24 are formed in the neck portion 22 of the body 12 as a result of twisting the body 12 during manufacturing of the device 10, as described above.

In one embodiment, the implement 18 and/or the neck portion 22 of the device 10 may include a color-changing material or compound that is configured to change color when contacted by water or cerumen. In that regard, a portion of the implement 18 or the neck portion 22 of the device 10, or both, may include a moisture indicator embedded or layered therein. The moisture indicator is configured to change color when placed in contact with moisture. When dry, the moisture indicator may be white or generally colorless. Once in contact with moisture, such as water or other fluids in the ear, the moisture indicator reacts and changes color. The change in color of the moisture indicator on the implement 18 and/or neck portion 22 of the device 10 indicates to the user that the device 10 has removed an amount of moisture and/or cerumen from the ear canal 11. The change in color also indicates to a user that the device 10 has been previously used. The absorbent nature of the implement 18 and/or the neck portion 22 may facilitate the transfer or wicking of moisture from surfaces of the ear canal 11 to the moisture indicator. The moisture indicator may be a pH indicator such as bromothymol blue, phenolphthalein, and methyl orange. However, the moisture indicator may be formed from other moisture indicating materials such as cobalt chloride, methyl violet, a cobalt-free indicator or a copper-based indicator, for example.

Figure 5A:
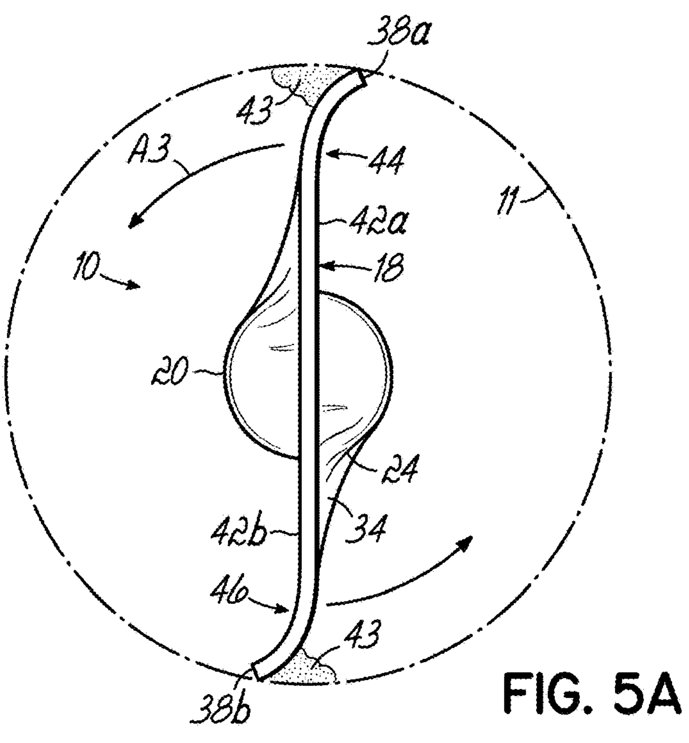
FIG. 5A is a diagrammatic front view of the hygiene device of FIGS. 1-4, illustrating the radial contraction of the hygiene device from use.
Figure 5B:
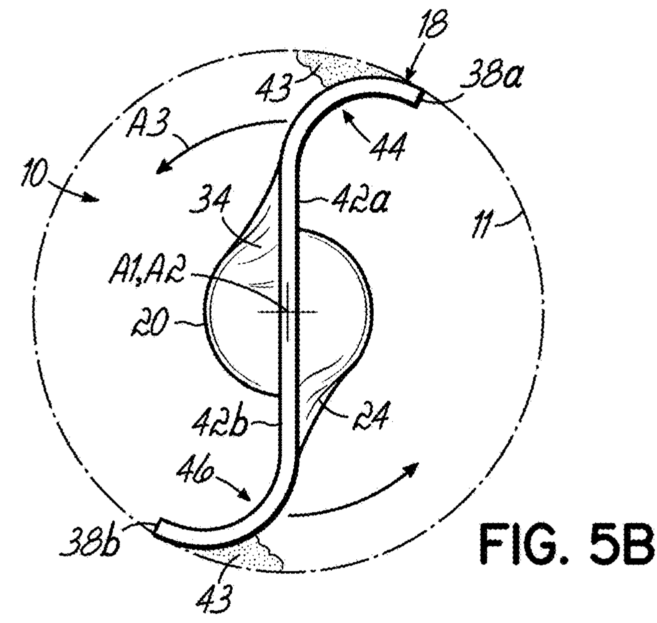
FIG. 5B is a view similar to FIG. 5A, further illustrating the radial contraction of the hygiene device from use.
Figure 5C:
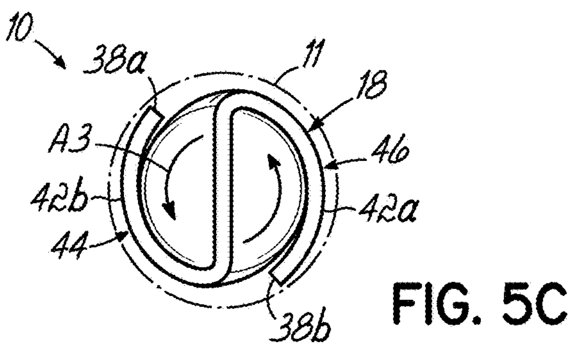
FIG. 5C is a view similar to FIGS. 5A and 5B, further illustrating the radial contraction of the hygiene device from use.
Figure 6:
FIG. 6 is a diagrammatic side view of a person's ear, illustrating the rotational movement of the hygiene device in the person's ear to remove cerumen and moisture from the outer one-third of the person's ear canal.

Turning now with reference to FIGS. 5A-6, the implement 18 is configured to radially deform as the device 10 is inserted and rotated in the ear canal 11 during use. In that regard, the implement 18 is deformable from a radially expanded configuration (e.g., FIG. 4) before use to a radially contracted configuration (e.g., FIGS. 5A-5C) during and after use. Use of the device 10 may likely result in the implement 18 being permanently deformed. As shown in FIG. 4, when in the radially expanded configuration, the body 32 of the implement 18 is generally flat or paddle shaped. However, it is possible that the body 32 of the implement 18 be slightly S-shaped in transverse cross-section when in the radially expanded configuration. In either case, the height H of the implement 18 is greater than the diameter D of the neck portion 22 of the body 12 of the device 10 when in the radially expanded configuration, as shown in FIG. 4. The implement 18 may be initially received in the ear in the radially expanded configuration. However, as the implement 18 is received further into the ear while being simultaneously rotated about its longitudinal axis A1, the implement 18 is eventually deformed to a radially contracted configuration, as shown in FIG. 5C.

FIGS. 5A-5C illustrate the implement 18 as it deforms to a radially contracted configuration during use. In that regard, a user inserts the device 10 into their ear, as generally shown in FIG. 6, while simultaneously rotating the device 10 about its longitudinal axis A1 using the handle 20, as indicated by directional arrows A3 in FIGS. 5A-6. The user may be instructed to rotate the device 10 toward their nose, as shown in FIG. 6. The rotational direction corresponds to the spiral crevices 24 formed in the device 10, so that rotating the device 10 tightens and closes the crevices 24 rather than opening them. Therefore, there may be a version of the device 10 for the right ear and the left ear, depending on the configuration of the spiral crevices 24.

As the device 10 is inserted into the ear and rotated, the implement 18 brushes or scrapes along the surfaces of the ear canal 11, wicking, gathering, and trapping cerumen and particulate matter 43 between the implement 18 and the surfaces of the ear canal 11, as shown in FIGS. 5A and 5B. Continued rotation of the device 10 within the ear canal 11 causes the implement 18 to collapse in a radially inward direction to become generally S-shaped. In particular, a first half 44 and a second half 46 of the implement 18 are curled about the axial center A2 of the device 10 in a direction opposite that of the rotational direction of the device 10. The first half 44 of the implement 18 extends from the axial center A2 of the device 10 to a first radially peripheral edge 38*a* and the second half 46 of the implement 18 extends from the axial center A2 of the device 10 to a second radially peripheral edge 38*b*. As the device 10 is rotated in a first rotational direction A3, the first half 44 and the second half 46 of the implement 18 are each curled in a rotationally opposite direction about the axial center A2 of the device 10. As a result, each half 44, 46 collapses or folds in a radial direction, moving the peripheral edges 38*a*, 38*b* of the implement 18 in a radially inward direction toward the axial center A2 of the device 10 to change the height H of the implement 18. As shown in FIG. 5C, when in the radially contracted configuration, the height H of the implement 18 is generally the same or smaller compared to the diameter D of the neck portion 22 of the device 10.

When in the radially contracted configuration, the implement 18 may become denser and function like a drill bit or auger bit to pull cerumen and particulate 43 out of the ear. That is, the cerumen and particulate 43 may be trapped within the folds of each half 44, 46 of the implement 18. Moreover, the spiral crevices 24 may also trap and remove cerumen and particulate matter 43 from the ear, similar to a drill bit or auger bit. When the device 10 is rotated, the crevices 24 close, thereby trapping any cerumen and particulate matter 43 contained within them. As the device 10 deforms into the radially contracted configuration, it becomes more resistant to collapsing along its longitudinal axis A1. In other words, the device 10 gains increased structural stability against axial compression as it deforms. Moreover, the implement 18 may be generally cone-shaped when in the radially contracted configuration. In that regard, the height H of the implement 18 may be greater near the base portion 34 of the implement 18 compared to the tip edge 36. To this end, the tip edge 36 of the implement 18 may form the apex of the cone shape.

The implement 18 is configured to collapse along the longitudinal axis A1 of the device 10 at a predetermined applied pressure to prevent ear trauma. In that regard, the implement 18 is configured to crumple or collapse under a predetermined applied pressure to prevent impaction of ear wax or damage to the ear canal 11. In other words, the structural integrity of the implement 18 fails before the implement 18 may injure the ear canal 11. To this end, the neck portion 22 of the device 10 may also be configured to crumple or collapse along the longitudinal axis A1 of the device 10 at a predetermined pressure to prevent ear trauma. The implement 18 may begin to collapse at relatively low compressive pressures, such as about 0.1 to about 0.5 pounds per square inch (psi), for example. As used herein, "about" means within +/−10%.

As briefly described above, the working length of the device 10 may be individually customized based on the measurement of an individual's ear canal 11. Other dimensions of the device 10 may also be tailored to the measurements of an individual's ear. For instance, the height H (FIG. 4) of the implement 18 may be sized to fit an individual's ear canal 11. In that regard, an audiologist may take measurements of an individual's ear canal 11, such as the length of the outer one-third and the diameter of the canal. At least the diameter measurement may be taken using a sizer plug, for example. The working length of the device 10 may then be sized to correspond to the length of the outer one-third of the person's ear canal 11. Additionally, the height of the implement 18 may be sized 1 to 2 mm larger than the diameter of the person's ear canal 11. This ensures that the implement 18 brushes against the surfaces of the ear canal 11 and may be deformed into the radially contracted configuration during use, as described above. The height H of the implement 18 may range from about 3 mm to about 18.5 mm, for example.

Figure 7:
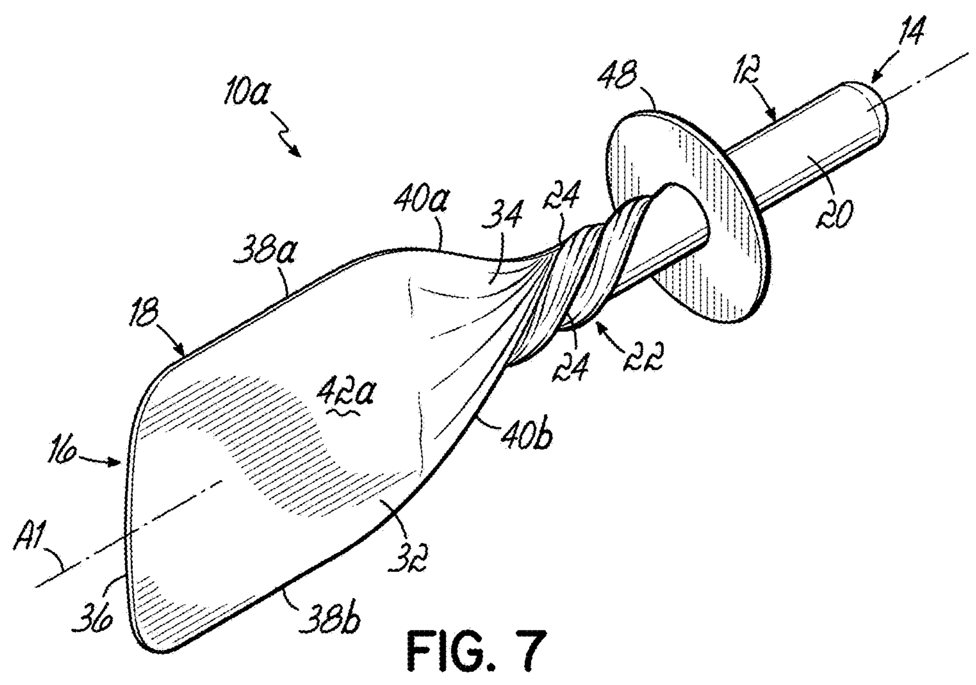
FIG. 7 is a perspective view of a hygiene device for cleaning an ear canal in accordance with another embodiment of the disclosure.
Figure 8:
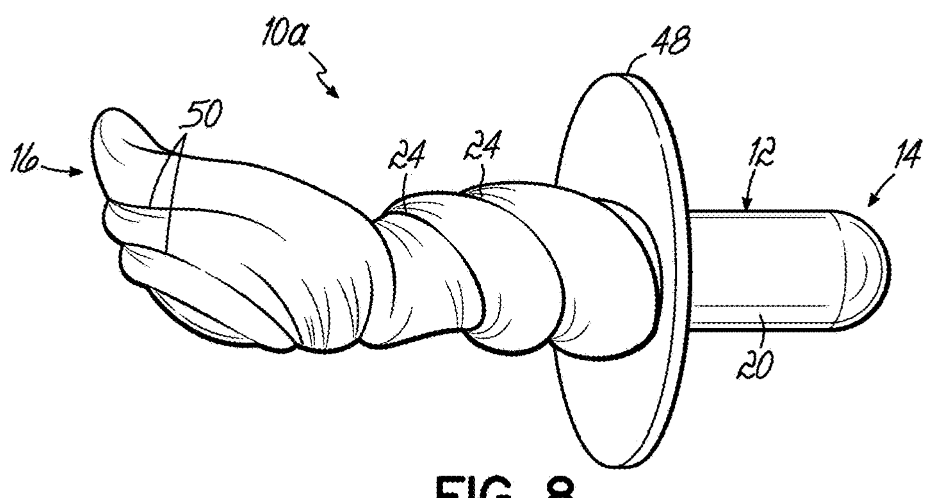
FIG. 8 is a side view of the hygiene device of FIG. 7, illustrating the hygiene device in a radially contracted configuration after use.

Referring now to FIGS. 7 and 8, an ear hygiene device ("device") 10*a* is shown in accordance with another embodiment of the disclosure. In that regard, like reference numerals represent like features compared to the embodiment of the device 10 described above with respect to FIGS. 1-6. The primary difference between the device 10*a* of this embodiment and the device 10 of the previously described embodiment is that the body 12 of the device 10*a* includes an annular flange 48 disposed between the neck portion 22 and the handle 20. The flange 48 is configured to limit insertion of the implement 18 into the ear canal 11. The flange 48 may be circular or oval in shape and extends circumferentially about the body 12 of the device 10*a*. The flange 48 may be sized to cover external parts of the ear, such as the concha, lobule, anti-helix, and helix, for example. In that regard, the flange 48 is configured to contact external parts of the ear and may be formed from the same material as the body 12 of the device 10*a*. Specifically, the flange 48 may be absorbent to absorb or remove water and other moisture from external parts of the ear. This may be important for hearing aid users to prevent the hearing aid receivers (speakers) from becoming wet and damaged. To this end, the flange 48 serves both a safety function and a cleaning function.

FIG. 8 illustrates the device 10*a* in the radially contracted configuration after use. As shown, the implement 18 is deformed, being collapsed in a radially inward direction from rotation of the device 10 within the ear canal 11. In that regard, FIG. 8 may be representative of the implement 18 after use for both embodiments of the device 10, 10*a*. As shown, the crevices 24, and in particular the spiral crevices 24 may continue from the neck portion 22 of the devices to the implement 18. Although the halves 44, 46 of the implement 18 collapse in a radially inward direction to become generally S-shaped, as described above, the halves 44, 46 of the implement 18 are generally crumpled. Deformation of the implement 18 during use results in new crevices 50 being formed in the implement 18. Cerumen and particulate 43 may be trapped within the new crevices 50 as they are formed.

Figure 9:
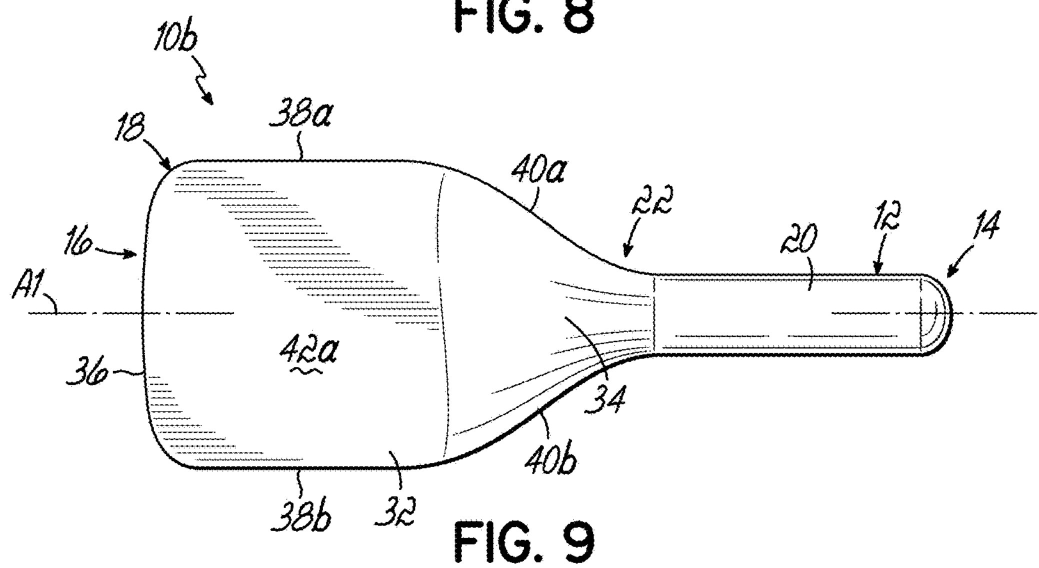
FIG. 9 is a perspective view of a hygiene device for cleaning an ear canal in accordance with another embodiment of the disclosure.

Referring now to FIG. 9, an ear hygiene device ("device") 10*b* is shown in accordance with another embodiment of the disclosure. Like reference numerals represent like features compared to the device 10 described in FIGS. 1-6. The primary difference between this embodiment of the device 10*b* and the previously described embodiment of the device 10 is that the device 10*b* is press-formed without spiral crevices 24. However, the device 10*b* may include small wrinkles and crevices in the neck portion 22 and the implement 18. The spiral crevices, along with other wrinkles and crevices, may be formed during the use of the device 10*b*. That is, rotation of the device 10*b* within the ear canal 11 not only radially deforms the implement 18 of the device 10*b*, as described above, but also forms spiral crevices that trap cerumen and particulate matter 43.

While the present disclosure has been illustrated by the description of specific embodiments thereof, and while the embodiments have been described in considerable detail, it is not intended to restrict or in any way limit the scope of the appended claims to such detail. The various features discussed herein may be used alone or in any combination within and between the various embodiments. Additional advantages and modifications will readily appear to those skilled in the art. The disclosure in its broader aspects is therefore not limited to the specific details, representative apparatus and methods and illustrative examples shown and described. Accordingly, departures may be made from such details without departing from the scope of the disclosure.

What is claimed is:

1. A device for removing and preventing the buildup of cerumen in an ear canal, the device comprising:

a body that extends between a distal end and a proximal end to define a longitudinal axis of the device, the body comprising:

an elongated handle at the proximal end of the body; and a neck portion that extends from the handle to a paddle implement at the distal end of the body, the neck portion including one or more crevices;

wherein the one or more crevices comprise one or more spiral crevices that extend circumferentially about the neck portion and along the longitudinal axis of the device; and the paddle implement including a flattened body having a width between a first flat surface and a diametrically opposed second flat surface and a height between radially peripheral edges of the paddle implement, the width of the paddle implement being less than a diameter of the neck portion;

wherein the paddle implement is configured to radially deform as the device is inserted and rotated in the ear canal during use, the paddle implement being deformable from a radially expanded configuration before use, wherein the height of the paddle implement is greater than the diameter of the neck portion, to a radially contracted configuration after use, wherein the diameter of the paddle implement is the same or smaller compared to the diameter of the neck portion.

2. The device of claim 1, wherein the body is formed of a biodegradable material.

3. The device of claim 1, wherein the paddle implement is S-shaped in transverse cross-section when in the radially contracted configuration.

4. The device of claim 1, wherein the paddle implement includes a first half that extends from the longitudinal axis of the device to a first radially peripheral edge and a second half that extends from the longitudinal axis of the device to a second radially peripheral edge, wherein the first half and the second half of the paddle implement are curled about the longitudinal axis of the device when in the radially contracted configuration.

5. The device of claim 4, wherein the first half and the second half of the paddle implement are each curled in a rotationally opposite direction about the longitudinal axis relative to a rotational direction of the device.

6. The device of claim 1, wherein the body of the device further comprises an annular flange disposed between the neck portion and the handle, the flange being configured to limit insertion of the paddle implement into the ear canal.

7. The device of claim 1, wherein the paddle implement is absorbent.

8. The device of claim 1, wherein the neck portion is absorbent.

9. The device of claim 1, wherein a portion of the paddle implement or the neck portion includes a color-changing material configured to change color when contacted by water or cerumen.

10. The device of claim 1, wherein at least one of the one or more crevices extends beyond the neck portion to the paddle implement.

11. The device of claim 10, wherein the at least one of the one or more crevices extends onto the first flat surface or the second flat surface of the paddle implement.

12. The device of claim 1, wherein the paddle implement is configured to collapse along the longitudinal axis of the device at a predetermined pressure.

13. The device of claim 12, wherein predetermined pressure is within a range of between about 0.1 to about 0.5 psi.

14. The device of claim 1, wherein the elongated handle includes a non-absorbent outer coating.

15. The device of claim 14, wherein the outer coating includes a hardness that is greater than a hardness of the body of the device.

16. The device of claim 1, wherein the paddle implement is configured to permanently radially deform as the device is inserted and rotated in the ear canal during use.

17. A method of using a device for removing and preventing the buildup of cerumen in an ear canal of a user, the method comprising:

providing the device, comprising:

a body that extends between a distal end and a proximal end to define a longitudinal axis of the device, the body comprising:

an elongated handle at the proximal end of the body; and a neck portion that extends from the handle to a paddle implement at the distal end of the body, the neck portion including one or more crevices;

wherein the one or more crevices comprise one or more spiral crevices that extend circumferentially about the neck portion and along the longitudinal axis of the device; and the paddle implement including a flattened body having a width between a first flat surface and a diametrically opposed second flat surface and a height between radially peripheral edges of the paddle implement, the width of the paddle implement being less than a diameter of the neck portion; and inserting the paddle implement into the ear canal;

rotating the device about the longitudinal axis of the device and in a direction toward a nose of the user to deform the paddle implement; and removing the paddle implement from the ear canal, wherein the paddle implement remains deformed.

18. A method of sizing a device for removing and preventing the buildup of cerumen in an ear canal, the method comprising:

measuring a diameter of the outer one-third of the ear canal; and selecting the device corresponding to the measured diameter of the outer one-third of the ear canal, the device comprising:

a body that extends between a distal end and a proximal end to define a longitudinal axis of the device, the body comprising:

an elongated handle at the proximal end of the body; and a neck portion that extends from the handle to a paddle implement at the distal end of the body, the neck portion including one or more crevices;

wherein the one or more crevices comprise one or more spiral crevices that extend circumferentially about the neck portion and along the longitudinal axis of the device; and the paddle implement including a flattened body having a width between a first flat surface and a diametrically opposed second flat surface and a height between radially peripheral edges of the paddle implement, the width of the paddle implement being less than a diameter of the neck portion;

wherein the height of the paddle implement is between 1 mm to 2 mm greater than the diameter of the outer one-third of the ear canal.

19. The method of claim 18, wherein a length of the neck portion and the implement defines a working length of the device, the method further comprising:

measuring a length of the outer one-third of the ear canal; and selecting the device corresponding to the measured length of the outer one-third of the ear canal, wherein the working length of the device is equivalent to the length of the outer one-third of the ear canal.

* * * * *